(12) United States Patent
Slycke et al.

(10) Patent No.: US 12,239,757 B2
(45) Date of Patent: Mar. 4, 2025

(54) SYSTEM AND METHOD FOR MOBILE SERVICE ROBOT SITE DISINFECTION

(71) Applicant: Loop Robots, Rijswijk (NL)

(72) Inventors: Per Slycke, Rijswijk (NL); Aswin Chandarr, Rijswijk (NL); Dimitrios Chronopoulos, Rijswijk (NL)

(73) Assignee: LOOP ROBOTS, Rijswijk (NL)

( * ) Notice: Subject to any disclaimer, the term of this patent is extended or adjusted under 35 U.S.C. 154(b) by 0 days.

(21) Appl. No.: 17/229,774

(22) Filed: Apr. 13, 2021

(65) Prior Publication Data

US 2024/0181109 A1 Jun. 6, 2024

(51) Int. Cl.
*A61L 2/10* (2006.01)
*A61L 2/24* (2006.01)
*B25J 9/16* (2006.01)

(52) U.S. Cl.
CPC ............... *A61L 2/24* (2013.01); *A61L 2/10* (2013.01); *B25J 9/1664* (2013.01); *A61L 2202/11* (2013.01); *A61L 2202/14* (2013.01); *A61L 2202/16* (2013.01); *A61L 2202/25* (2013.01)

(58) Field of Classification Search
CPC ..................................... A61L 2/10; A61L 2/24
See application file for complete search history.

(56) References Cited

U.S. PATENT DOCUMENTS

2022/0001061 A1* 1/2022 Hoang ..................... A61L 2/24

* cited by examiner

*Primary Examiner* — Kevin Joyner
(74) *Attorney, Agent, or Firm* — The Watson IP Group, PLC; Jovan N. Jovanovic

(57) ABSTRACT

Systems and methods for robot-executed site disinfection are provided, employing an autonomous robot equipped with a germicidal light source. In an area that is already mapped with a pre-defined trajectory, the robot may generate a map of delivered dosage and regions of UVC shadows when the robot moves in the environment. Alternatively, the robot may generate a trajectory to be followed, optimized to reduce shadows and minimize electrical energy usage. In an area already mapped, the robot may generate a map of delivered dosage and of shadows. Alternatively, the robot may generate a trajectory to disinfect surfaces based on an area map while reducing shadows and minimizing electrical energy usage. In an unmapped area, the robot may employ an exploration strategy to generate a trajectory to create a map of the area, while simultaneously performing disinfection of surfaces using a minimum amount of electrical energy.

20 Claims, 15 Drawing Sheets

| Distance to lamp, $l$ [cm] | 25 | 50 | 75 | 100 | 150 | 200 | 250 |
|---|---|---|---|---|---|---|---|
| Sensor output [mW/cm²] | 3.20 | 1.53 | 0.92 | 0.60 | 0.31 | 0.19 | 0.13 |
| Estimated radiance [mW/cm²] | 5.14 | 1.85 | 1.01 | 0.64 | 0.31 | 0.19 | 0.13 |
| Lamp power [W] | 85.7 | 81.5 | 86.2 | 89.9 | 93.9 | 100.0 | 102.4 |

FIG. 4

SYSTEM AND METHOD FOR MOBILE SERVICE ROBOT SITE DISINFECTION

TECHNICAL FIELD

The present disclosure is related generally to mobile service robots and, more particularly, to systems and methods for disinfection using same.

BACKGROUND

There are many environments wherein repeatable, reliable and verifiable disinfection of indoor spaces is required. For example, in the hospital environment, preventing Hospital Acquired Infections (HAI) is an ongoing challenge that is critical to patient safety. In addition to the patient cost, the associated financial costs are enormous. In acute care hospitals in the U.S. alone, such costs are approximately 97-147 Billion USD annually. One in ten patients worldwide is infected by an antibiotic-resistance pathogen while being treated in a hospital. This statistic does not include infections by viruses, such as SARS, MERS, SARS-COV-2 or influenza. HAI lead to 3 million infections in the USA alone, causing 48.000 preventable deaths each year.

Ultra-violet C (UVC) light from low-pressure mercury lamps, emitting strong radiation at 253.7 nm, is a well-known technology for inactivating pathogens. The germicidal efficacy of UVC is due to the fact that UVC directly disrupts the DNA or RNA in the pathogen. When enough damage is caused to the RNA or DNA, the pathogen can no longer multiply and is thus inactivated. UVC has many advantages over traditional methods for surface and room scale disinfection. It does not use chemicals and therefore does not cause resistance in pathogens or harm to the environment or personnel carrying out the disinfection process. Moreover, unlike some manual touch disinfectants like chlorine and non-touch disinfectants like hydrogen-peroxide vapor that can damage materials and surfaces, UVC like does not leave any residues and does not damage materials at low dosages.

Typical required UVC doses to achieve a desired reduction in active pathogens are shown in the following table in mJ/cm2. This table is from Malayeri, Adel & Mohseni, Madjid & Cairns, Bill. (2016). Fluence (UV Dose) Required to Achieve Incremental Log Inactivation of Bacteria, Protozoa, Viruses and Algae. IUVA News. 18. 4-6.

| Name | Log1 | Log2 | Log3 | Log4 |
|---|---|---|---|---|
| S Aureus (MRSA) | 4.50 | 7.20 | 8.80 | 10.00 |
| S Aureus (MSSA) | 4.40 | 5.80 | 6.40 | 7.30 |
| Acinetobacter Baumanii | 1.80 | 3.60 | 6.20 | 9.00 |
| Pseudomonas aeruginosa (MDR) | 1.50 | 2.60 | 3.80 | 5.00 |
| Enterococcus faecium | 7.00 | 9.00 | 11.00 | 13.00 |
| Enterococcus faecalis | 3.70 | 8.00 | 14.00 | 18.00 |
| Norovirus | 10.00 | 15.00 | 22.00 | 27.00 |
| Klebsiella terrigena | 3.60 | 6.40 | 9.30 | 12.00 |
| Sars Cov2 | 3.00 | 5.00 | 10.00 | 15.00 |
| Clostridium difficile | 16.00 | 34.00 | 46.00 | 62.00 |

Despite the many advantages of UVC, it is not yet widely applied because of a few key challenges. UVC light is only germicidal on surfaces that are irradiated by the UVC light. Any surfaces in shadow from the UVC light will not be disinfected. In addition, UVC is only germicidal if an adequate dosage is delivered to each surface that needs to be disinfected. The required dosage is different for each pathogen, since each pathogen exhibits a unique level of sensitivity to damage from UVC light. For this reason, UVC lamps used to disinfect surfaces and rooms in a healthcare setting have been designed to be movable in an attempt to reduce shadows and get closer to objects that need to be disinfected.

However, UVC lamps consume very significant amounts of electrical energy. A typical moveable UVC system is powered from an electrical outlet and consumes about 1-2 kW of electrical energy and needs to be powered for a significant amount of time (e.g., 30-60 min) to try to reach sufficient UVC dose delivered to space and surfaces furthest away from the lamps. For each disinfection, an operator can typically move the UVC lamps around a few times in a room to try to eliminate any shadows caused by objects in a room, such as a bed, chair or equipment. This is a laborious and error prone process. Recently, leveraging mobile service robot technology, several mobile robots have been developed that can automate the process of moving the UVC lamps around in the room to several locations, to minimize the amount of shadows and speed up operations somewhat. These systems however are limited in their use because the operation time is very limited (typically around 2 hours) and the robot is required to carry very large batteries. This results in robot UVC systems being expensive, heavy and slow to charge before being able to carry out a subsequent disinfection cycle.

Germicidal UVC lamps can be manufactured via different methods and incorporating different technologies. For example, germicidal lamps may be high pressure mercury lamps, amalgam lamps with specific properties or may use different mechanisms all together to generate (UV) light. For example, LEDs can be used to generate radiation at wave lengths other than 253.7 nm (which is specific for low pressure mercury lamps). In addition, far UVC lamps operating at 222 nm have also been shown to have germicidal effects. In this disclosure, UVC lamps should be construed to include all of these types of lamps and any other lamp technology that has a germicidal effect.

In addition, current systems do not provide accurate measurements or proof that each surface of interest for disinfection has received an adequate dosage of UVC radiation to guarantee effective inactivation of a targeted reduction in active pathogens, typically expressed as a log reduction.

In addition, current mobile robot UVC disinfection systems require extensive prior mapping of a space to allow the robot to navigate and disinfect the space. Prior mapping in such systems is a lengthy process requiring technical knowledge and is not practical for easy and flexible use in, for example, a hospital setting. Furthermore, current mobile robot UVC disinfection systems require prior manual path planning after mapping. This process is laborious and error prone and is not optimized for reduction of UVC shadows or minimizing power use to guarantee sufficient UVC dosage delivered to achieve disinfection or time for execution of disinfection. The requirement of prior mapping and prior path planning prevents flexible and easy deployment of such a robot disinfection system. In addition, current UVC disinfection systems typically deliver a significant excess amount of radiation, thereby not only wasting energy but potentially also negatively affecting UVC-sensitive surfaces and materials in the room, e.g., some types of plastics.

Moreover, current mobile robot UVC disinfection systems employ standard mobile robot path planning methods and avoid navigating close to surfaces in a room. This practice wastes UVC radiation energy and requires more irradiation time and energy to achieve a specified disinfection log reduction.

Before proceeding to the remainder of this disclosure, it should be appreciated that the disclosure may address some of the shortcomings listed or implicit in this Background section. However, any such benefit is not a limitation on the scope of the disclosed principles, or of the attached claims, except to the extent expressly noted in the claims.

Additionally, the discussion of technology in this Background section is reflective of the inventors' own observations, considerations, and thoughts, and is in no way intended to be, to accurately catalog, or to comprehensively summarize any prior art reference or practice. As such, the inventors expressly disclaim this section as admitted or assumed prior art. Moreover, the identification or implication herein of one or more desirable but unfollowed courses of action reflects the inventors' own observations and ideas, and should not be assumed to indicate an art-recognized desirability.

BRIEF DESCRIPTION OF THE SEVERAL VIEWS OF THE DRAWINGS

While the appended claims set forth the features of the present techniques with particularity, these techniques, together with their objects and advantages, may be best understood from the following detailed description taken in conjunction with the accompanying drawings of which:

FIG. 4 is a chart showing example measurements for a particular light source and reflector combination can be seen in accordance with an embodiment of the disclosed principles;

DETAILED DESCRIPTION

Figure 1:
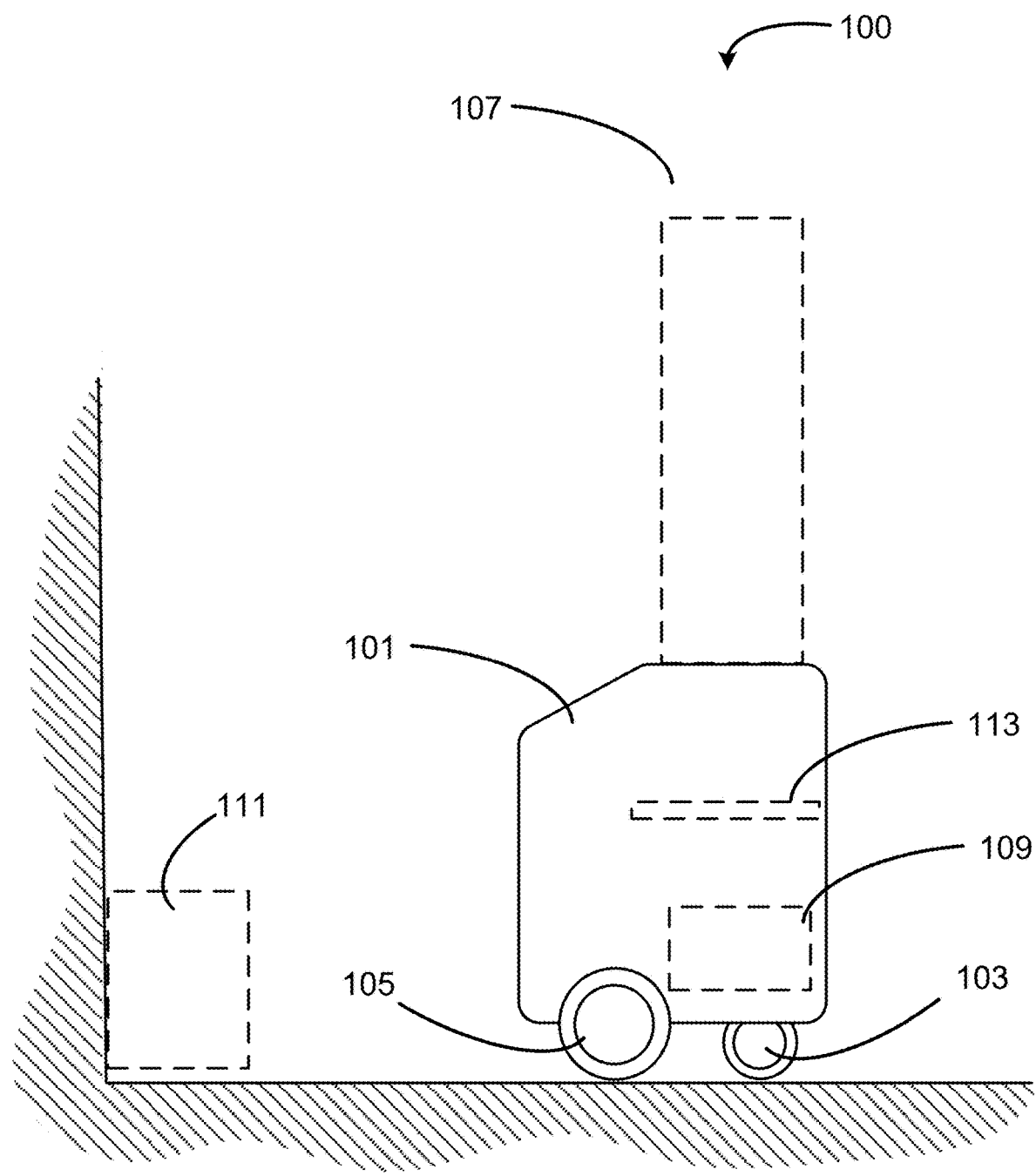
FIG. 1 is a schematic drawing of an example disinfection robot within which embodiments of the disclosed principles may be implemented.

Before presenting a detailed discussion of embodiments of the disclosed principles, an overview of certain embodiments is given to aid the reader in understanding the later discussion. As noted above, many situations and environments require repeatable, reliable and verifiable disinfection of indoor spaces. These include, most critically, hospital and other healthcare environments, although other environments such as convalescent and food preparation environments also require high hygienic standards and minimum microbial contamination to avoid adverse human health effects.

While UVC light from low pressure mercury lamps emitting at 253.7 nm is known for inactivating pathogens at appropriate dosage levels, UVC is not yet widely applied due to shadow effects, dosage delivered uncertainty, slow charging of mobile light sources, high electrical energy consumption, and consequent limited operation time, and lack of verification and flexible and fast deployment of mobile robots requiring prior mapping of areas to disinfect.

In an embodiment of the disclosed principles, a mobile service robot running appropriate software and algorithms mitigates the described problems by minimizing the amount of electrical energy needed to disinfect surfaces and objects of interest using UVC light by accurately modelling the precise amount of UVC dosage delivered to each surface in a room, to provide accurate estimates of active pathogen reduction to ensure inactivation of the pathogen of interest and by careful automated planning of the path the robot should take to achieve these objectives with minimum robot movement and minimum use of electrical energy.

The described process executed by the robot includes an offline phase and an online or active phase. The offline phase, in an embodiment, entails generation of a power distribution model per lamp, measuring the pose (position and orientation) of the light sources with respect to the CRP (central reference point) of the robot, and in some cases the generation of an occupancy map (2D or 3D) of the operational environment.

The online phase, in an embodiment, executes autonomous path planning to deliver required dosage on all surfaces of interest in a given spatial map. Exemplary steps include generation of a global disinfection costmap, clustering of curves into surface regions, trajectory planning to disinfect every surface region, and verification of dosage delivered on surface regions.

The techniques described may also include energy efficient exploration for disinfection of unknown area, computer vision (CV) for detection of surfaces and surface properties, closed loop disinfection using UVC sensors with a wireless connection to the robot, whether directly or indirectly, and computation of shadow regions after a disinfection task. Additional and alternative features will become more apparent below.

For purposes of this disclosure, the following terms should be understood to have the respective meaning listed after each term:

Spatial Occupancy Map: A 2D (x,y) or 3D (x,y,z) grid of a given resolution where each cell is marked as an obstacle, free space or unknown space.

Path: A set of points in 2D (x, y, theta) with reference to an origin of a map (2d or 3d).

Trajectory: A path with time stamp for each point.

Global Dosage Delivery map: Same dimensions as a Spatial Occupancy Map, where every cell has an additional value of the dosage (mJ/cm2) of UVC energy received at that location, also to be interpreted as a map where disinfection has been achieved by delivery of a minimum required dosage of UVC radiation to achieve a desired log reduction of a pathogen of interest and where areas can be identified that have not been disinfected because insufficient dosage was delivered.

Robot exploration: Motion of a mobile robot in a previously unknown area to create a spatial occupancy map autonomously.

With this overview in mind, and turning now to a more detailed discussion in conjunction with the attached figures, the techniques of the present disclosure are illustrated as being implemented in or via a suitable device environment. Thus, for example, FIG. 1 illustrates an example disinfection robot within which embodiments of the disclosed principles may be implemented. It will be appreciated that other device types may be used.

In the illustrated embodiment, the disinfection robot 100 includes a base 101, which is supported, driven and steered by wheels 103, 105. The disinfection robot 100 includes a light tower 107, which holds one or more UVC emitting lights. It will be appreciated that the disinfection robot 100 may include UVC emitting lights in other positions in addition to or instead of the light tower 107.

The disinfection robot 100 includes a power source 109 such as a battery, for powering the navigation of the disinfection robot 100 as well as the one or more UVC emitting lights. A wall charging station 111 may be provided for periodically recharging the power source 109. The disinfection robot 100 further includes a processor system 113 for executing the robot-based activities discussed herein. Necessary or desirable peripheral systems such as sensors, LIDAR sensors, cameras, motion tracking sensors, computer memory, latches, switches, antennas, communications facilities and so on are also included in the disinfection robot 100 but are omitted from the figure for clarity.

As noted above, the disinfection robot 100 provides autonomous UVC-based disinfection of surfaces in a region, including previously known (mapped) and previously unknown (not mapped) areas, with at least a predetermined dosage of UVC light using a minimum amount of electrical power. The process can be viewed as having three different situations, depending on if a map of the region is available or not. The first includes estimation of dosage received at every point on a given 2D or 3D spatial map when following a pre-determined planned trajectory, but taking into account the actually executed trajectory by the robot, taking into account for example avoidance of obstacles not included in the pre-determined planned trajectory. This part includes detection of shadows on a 3D map based on the configuration of UVC light sources.

Secondly, when a robot is in a previously known environment (with a fully mapped area in 2D or 3D), a motion trajectory is automatically generated for driving of the mobile robot to deliver the required dosage level at all possible regions of interest, using the least amount of electrical energy. This also includes a plan for controlling the UVC light sources (e.g., to switch them on and off automatically or to dim the power transmitted) at specific regions of the trajectory to save power. This motion trajectory can (optionally) be optimized to not deliver more than a maximum amount of dosage, to protect materials from overexposure.

Thirdly, when a robot is in a previously unknown area, a navigation schedule (trajectory) is generated to deliver a required dosage to all accessible surfaces using the least possible electrical energy, while building the map simultaneously. This stage is termed Disinfection Via Autonomous Simultaneous Localization and Mapping (DiVASLAM).

In each situation, the system identifies objects and surfaces of interest to disinfect in a given area. This also includes identifying material and surface properties that can influence UVC disinfection efficiency. Closed loop disinfection is optionally executed using wireless UVC sensors in the room, communicating with the robot directly or indirectly via another network such as the internet, so the robot behavior can be optimized with direct data from the UVC sensors in order to update the power distribution model of the lamps if needed based on data from the UVC sensors. Accurate computation of shadows or regions where the UVC light cannot reach is also useful in ensuring as complete disinfection as possible while tracking areas not likely to have been disinfected.

With respect to estimation of dosage map given a spatial occupancy map, this may be accomplished in two phases. These include an offline phase and an online phase. In the offline phase, a power distribution model per lamp is first generated. The pose (position and orientation) of the light sources is then quantified with respect to the CRP (Central Reference Point) of the robot.

The objective is to estimate the spectral illumination power (at 254 nm wavelength) received by a point at a position (x,y,z)m relative to the robot. The orientation of the point ($\alpha$) if it is close to being perpendicular or parallel to the light source is also taken into account. The spectral illumination power is measured in mW/cm$^2$. The starting point is a reference spectral power from the datasheet of the light source. The manufacturer specifies the received illumination power at 1 m distance from the lamp. In cases where this is a cylindrical TL lamp, this value should be approximately the same 360 degrees around the lamp at a fixed distance.

This cannot be directly used in practice as reflectors are often used to shape the power distribution of the lamp. Since it is not possible to completely model the reflector properties and the combination of the lamp and reflector (with distance between them), the power distribution of the light source and reflector together is modeled based on experimental power measurements. First, a mathematical model of illumination power distribution for a single light source is created. The power received varies if a point is parallel or perpendicular to the light source. Based on this two models are obtained.

Figure 2:
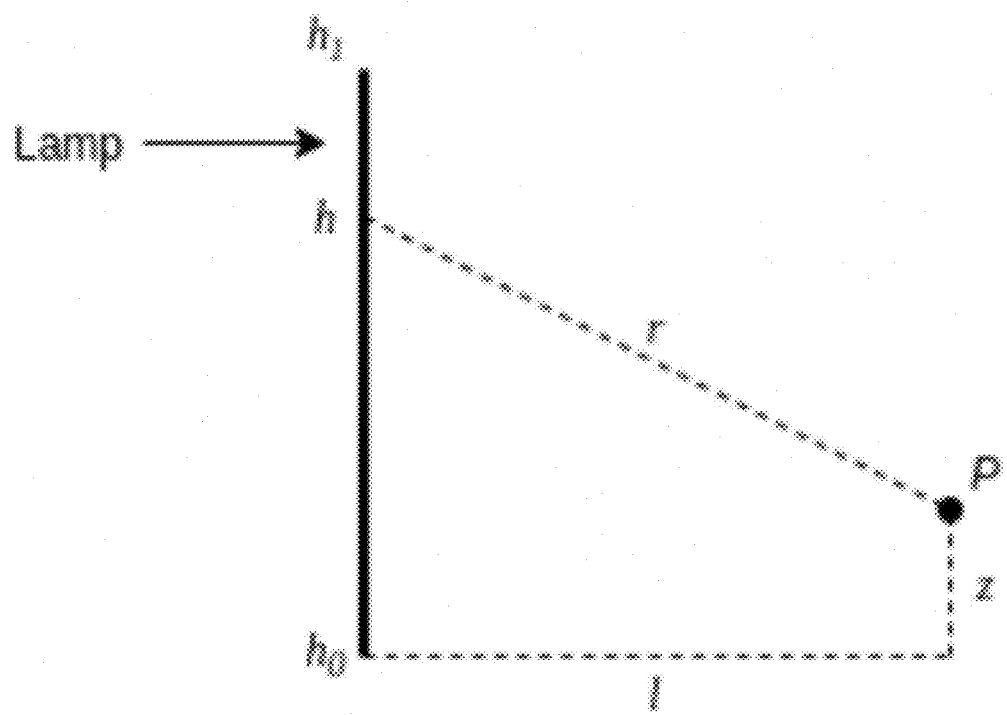
FIG. 2 is a 2D plan view of a light path and impingement angle when a target point P is on a surface parallel to the light source in accordance with an embodiment of the disclosed principles.

When the target point P is on a surface parallel to the light source as shown in FIG. 2, the power received at the point P on the surface at a distance "l" from the light source can be estimated as the integral over "h" per Equation 1 below:

$$I_{total} = \left[ \frac{P_{total} \cdot \arctan\left(\frac{h}{l}\right)}{4\pi l H} \right]_{h_{0-z}}^{h_{1-z}}$$

This provides the total power received at a surface parallel to the light source.

Figure 3:
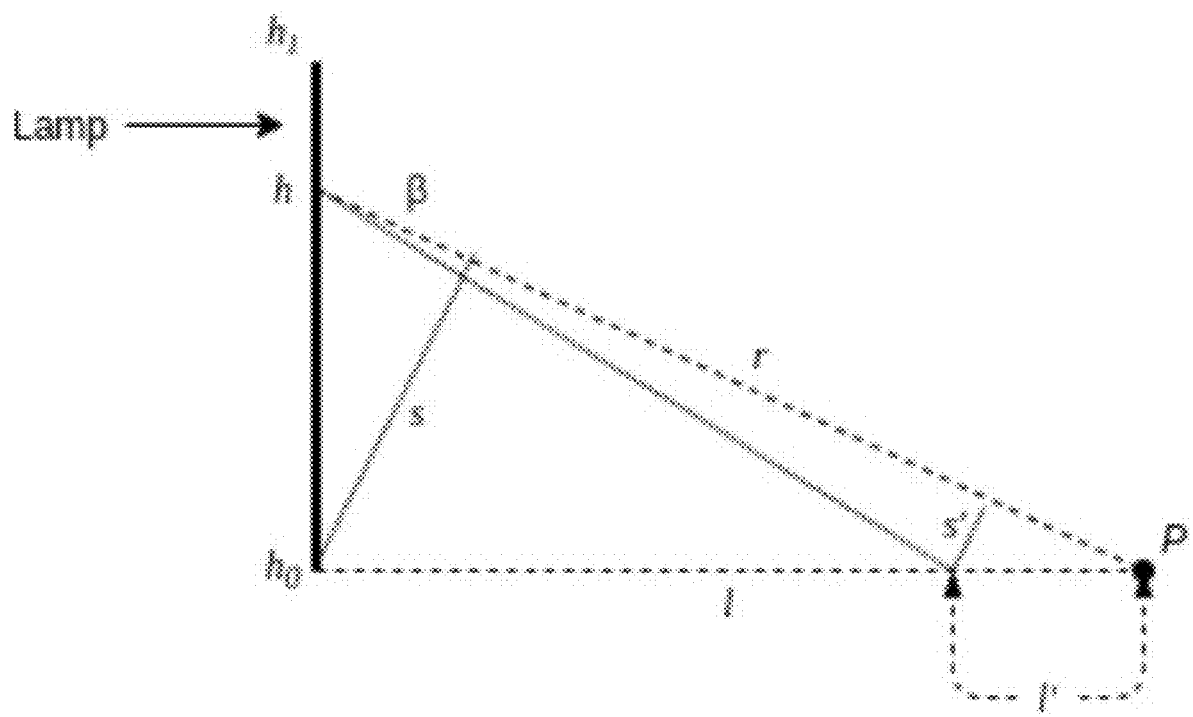
FIG. 3 is a 2D plan view of a light path and impingement angle when a target point P is on a surface perpendicular to the light source in accordance with an embodiment of the disclosed principles.

When the target point is on a surface perpendicular to the light source, as shown in FIG. 3, the power received at such a point on the surface at a distance "l" can be estimated as the integral over "h" per Equation 2 below:

$$I_{surface} = \frac{P_{total}}{4\pi H} \cdot \left[\frac{1}{\sqrt{h^2+l^2}}\right]_{h_{1-z}}^{h_{0-z}}$$

This is then the total power received at a surface perpendicular to the light source.

The parameters of a light source here are the total power ($P_{total}$) and the height (H) of the light source. While H can be directly obtained from the specification datasheet, the $P_{total}$ including the reflector is estimated from experimental measurements. The change in received power for points at the same distance (l) but different angle (γ) caused due to the addition of reflector can be modeled as an angular yield factor in a cubic function as per Equation 3 below:

$$\eta_{angle} = 1 - K\gamma^2$$

Where the factor "K" can be identified experimentally.

Secondly a digital UVC power sensor measuring mW/cm2 of UVC of the appropriate wavelength is used. This can be any calibrated digital UVC meter available on the market. The $P_{total}$ and K are estimated experimentally as noted above.

Keeping a γ=0, multiple measurements are made at each distance for varying distances. Averaging of the multiple measurements at every distance may be used to remove sensor process noise. Example measurements for a particular light source and reflector combination can be seen in the chart 400 of FIG. 4.

The Lamp power is calculated for every distance using Equation 4 (the inverse of Equation 1) which is:

$$P_{total} = I_{total} \left[\frac{4\pi lH}{\arctan\left(\frac{h}{l}\right)}\right]_{h_{0-z}}^{h_{1-z}}$$

The total irradiated power of the light source including both the lamp and the reflector is then obtained as the average of $P_{total}$ at various distances. In an example, $P_{total}$ Was estimated to be 91 W.

Figure 5:
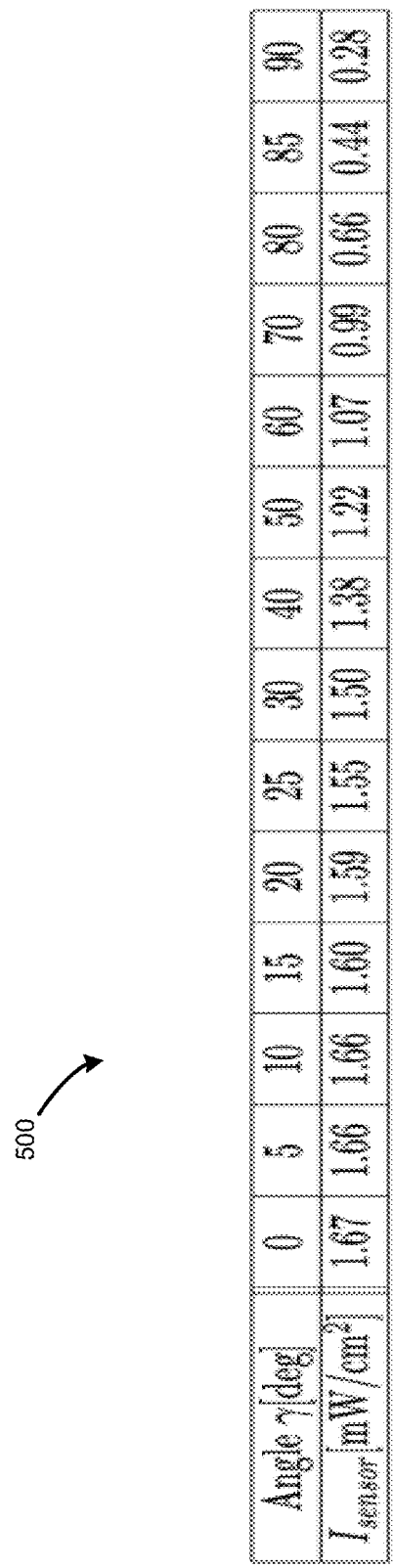
FIG. 5 is a chart showing example angle and intensity measurements in accordance with an embodiment of the disclosed principles.

The angular yield factor of Equation 3 can be estimated by performing power measurements at various γ at a given distance. Example measurements are shown in the chart 500 of FIG. 5. Based on these measurements, the K for this light source was estimated at 0.32.

Figure 6:
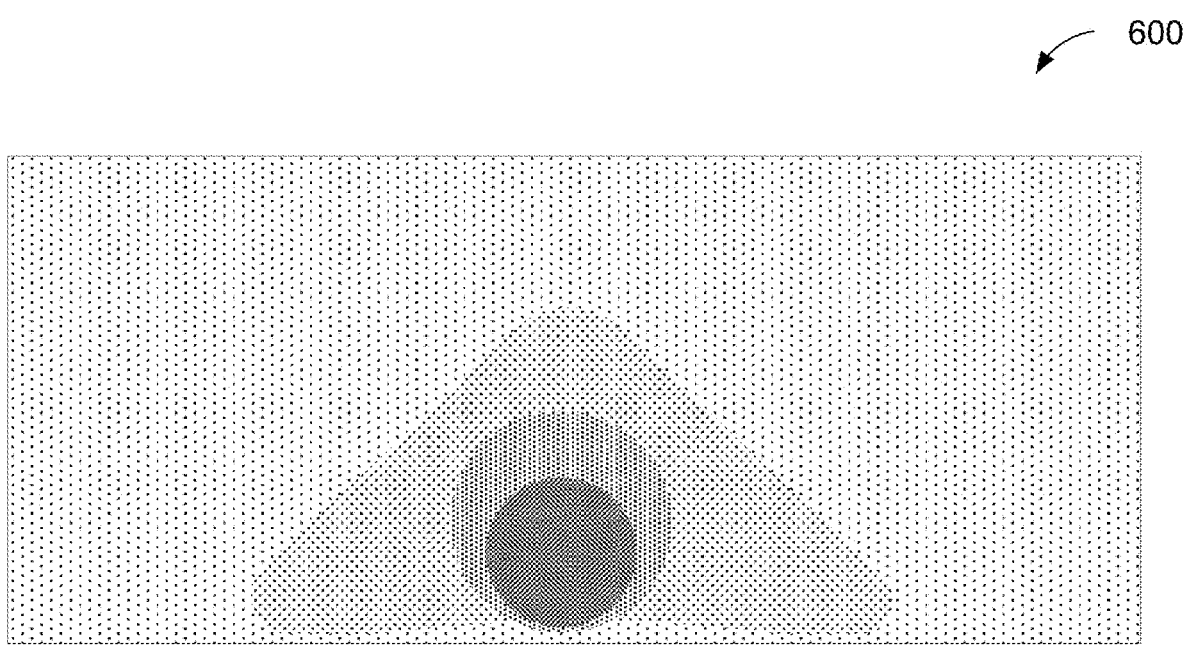
FIG. 6 is a model plot of power received at varying horizontal position for a particular height in accordance with an embodiment of the disclosed principles, wherein higher density shading identifies higher relative power values.

With Equations 1-3, the received illumination power at any point at distance (x,y,z) m from the light source, lying on a surface either parallel or perpendicular to the light source can be estimated. This model can be visualized as power received at varying (x,y) for a particular height as shown in the plot 600 of FIG. 6, wherein higher density shading identifies higher relative power values.

This process is repeated for each light source independently, and the model may be experimentally verified by measuring the UVC Irradiance (mW/cm²) using a calibrated UVC radiometer. This is preferably verified at various distances and orientations from the lamp. A lookup table is then created based on such experimental measurements, which can also be used as a static irradiance model of a single lamp.

Figure 7:
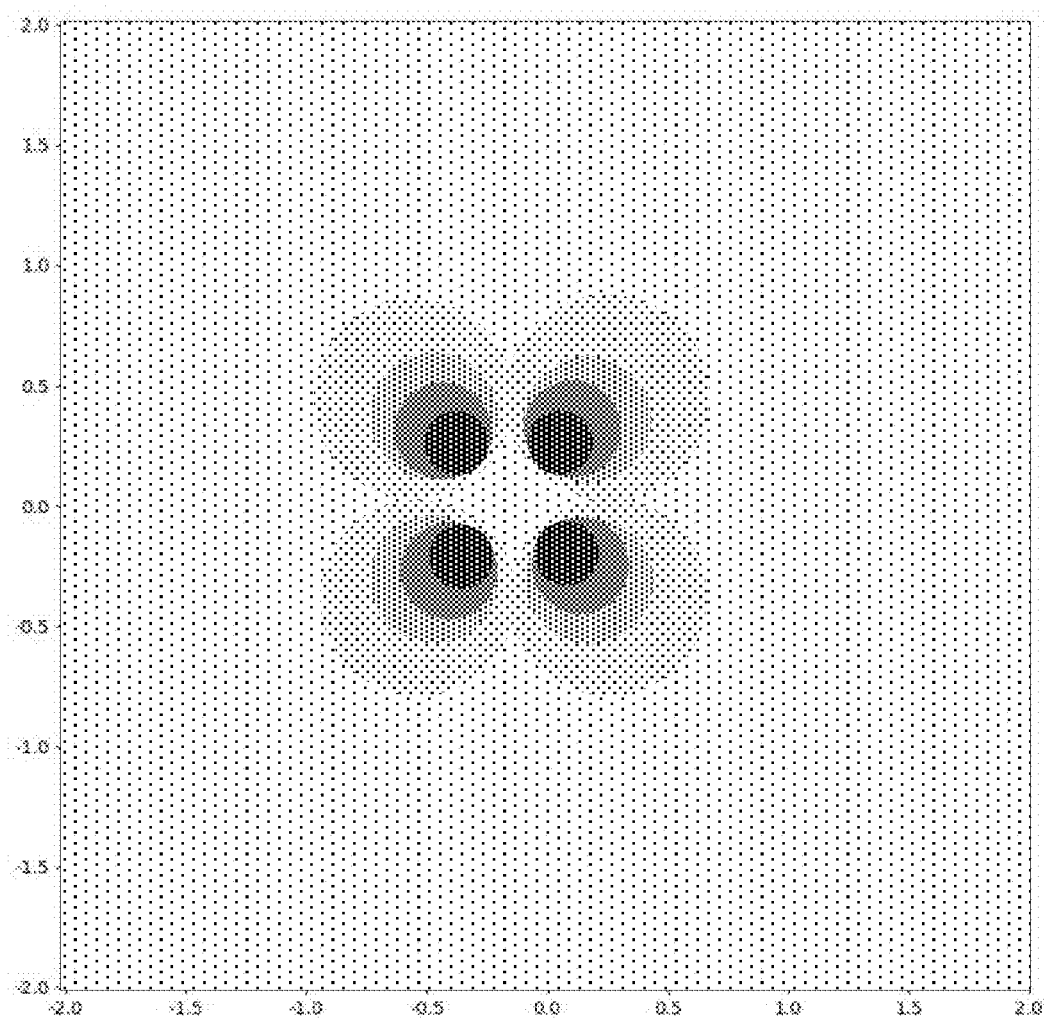
FIG. 7 is a model plot of illumination distribution for a robot with 4 light sources arranged at the corners of a square facing 45 degrees from the center in accordance with an embodiment of the disclosed principles.

With respect to measuring the pose (position and orientation) of the light sources with respect to the center point of the robot (CRP), at first the relative poses (positions and orientations) of the light sources with respect to the center of robot (CRP) are measured. Since the received illumination power is additive in nature, the power distribution models of individual light sources (se FIG. 6) can be superimposed on each other. This superposition is performed after transforming the single source power model based on the pose relative to robot CRP. An example illumination distribution model for a robot with 4 light sources arranged at the corners of a square facing 45 degrees from the center can be seen in the plot 700 of FIG. 7. The creation of a power distribution model for each lamp and measuring the pose of the light sources with respect to the CRP of the robot are performed once for each robot light source configuration.

Figure 8:
FIG. 8 is an example 2D occupancy grid map in accordance with an embodiment of the disclosed principles.

The creation of an occupancy map (2D or 3D) of the operational environment is optionally performed once per an area/location that has to be disinfected. This aids in planning the motion of the robot and also in estimating the UVC dosage delivered at every point. The output of this process will yield an occupancy grid map, which segments a grid map into occupied, free or unknown segments. An example 2D occupancy grid map 800 is shown in FIG. 8.

Figure 9:
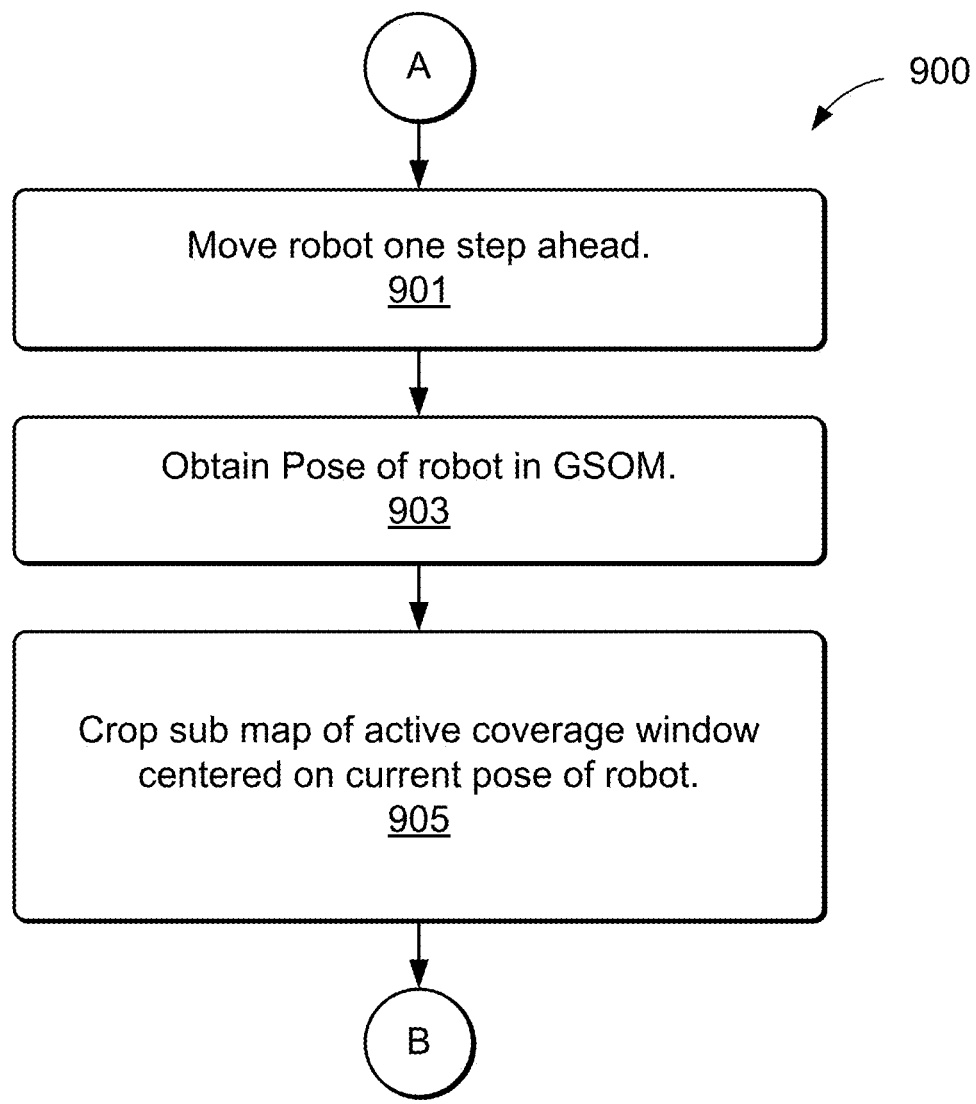
FIG. 9 is a flow chart of a process in accordance with an embodiment of the disclosed principles.
Figure 10:
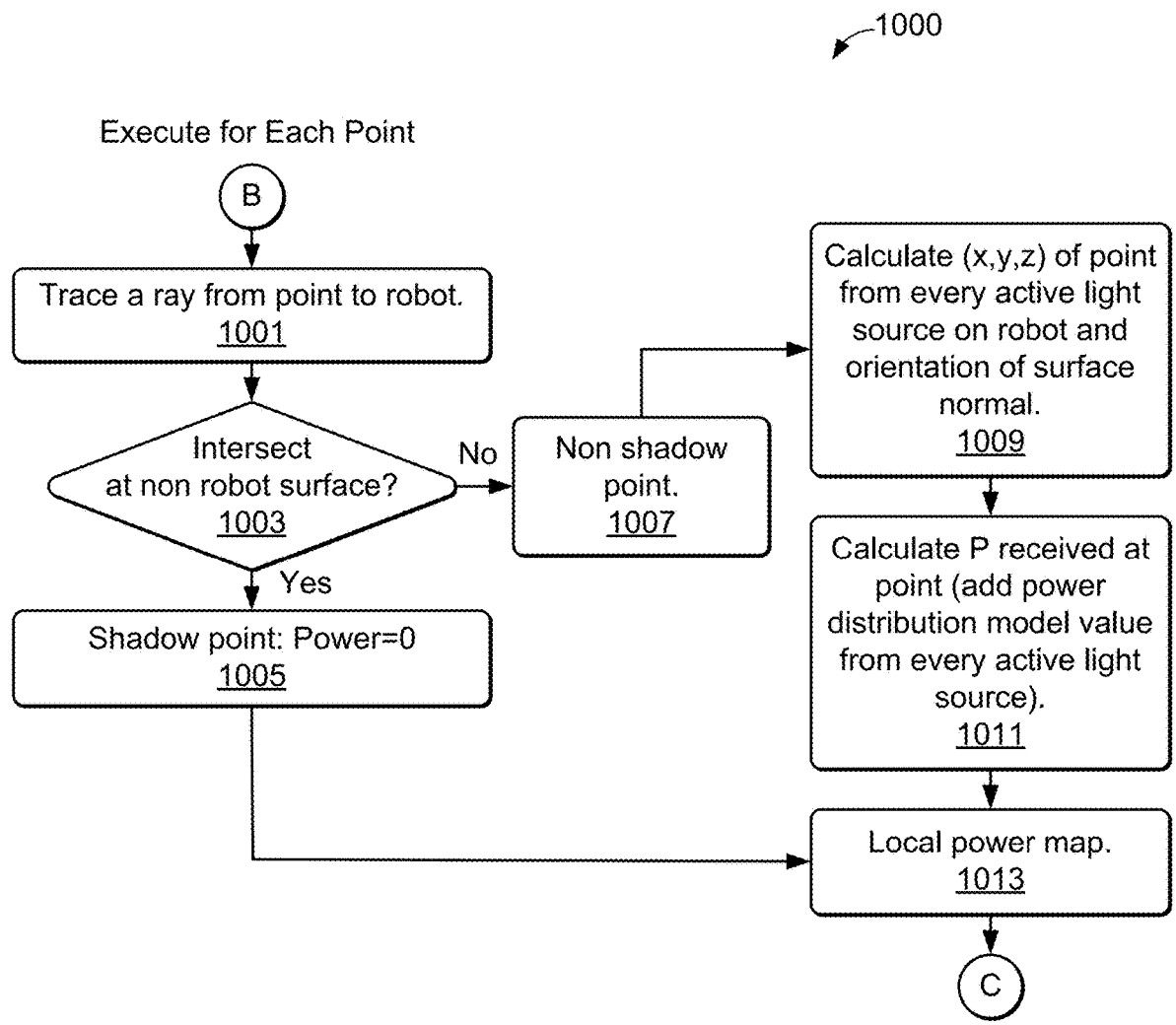
FIG. 10 is a continuing flow chart the process in accordance with FIG. 9.

As noted above, there is an offline phase, which has been discussed above, as well as an online phase. In the online phase, which may recur, the system generates a map of complete UVC dosage delivered in the environment when the robot is navigating in a manually predefined path programmed on the robot before it is used. The flow charts extending over FIGS. 9-11 show a first process for generating the global dosage map when following a programmed route.

At stage 901 of the process 900, the robot is moved one step ahead, and the pose of the robot in the GSOM (global spatial occupancy map) is then obtained at stage 903. In one aspect of the invention, to limit computational resources, a sub map of the active coverage window (l×w×h) is cropped from the GSOM centered around current pose of the robot at stage 905, after which the process flows to point B in FIG. 10. At stage 1001 of the continued process 1000, which is executed for each point, a ray is traced from the current point to the robot UVC light source(s). If at stage 1003 it is determined that the ray intersects a non-robot surface, then the process 1000 flows to stage 1005 wherein the point is flagged as a shadow point receiving zero UVC power at this step.

Otherwise, the point is flagged as a non-shadow point for this step in state 1007 and, in stage 1009, the position of the point relative to each active light source on the robot is calculated and the orientation of the surface normal is stored. At stage 1011, the power received at the point is calculated by summing the power distribution model value from every active light source. Using a value of zero for each known shadow points and the calculated power values for non-shadow point, a local power map is generated at stage 1013.

Figure 11:
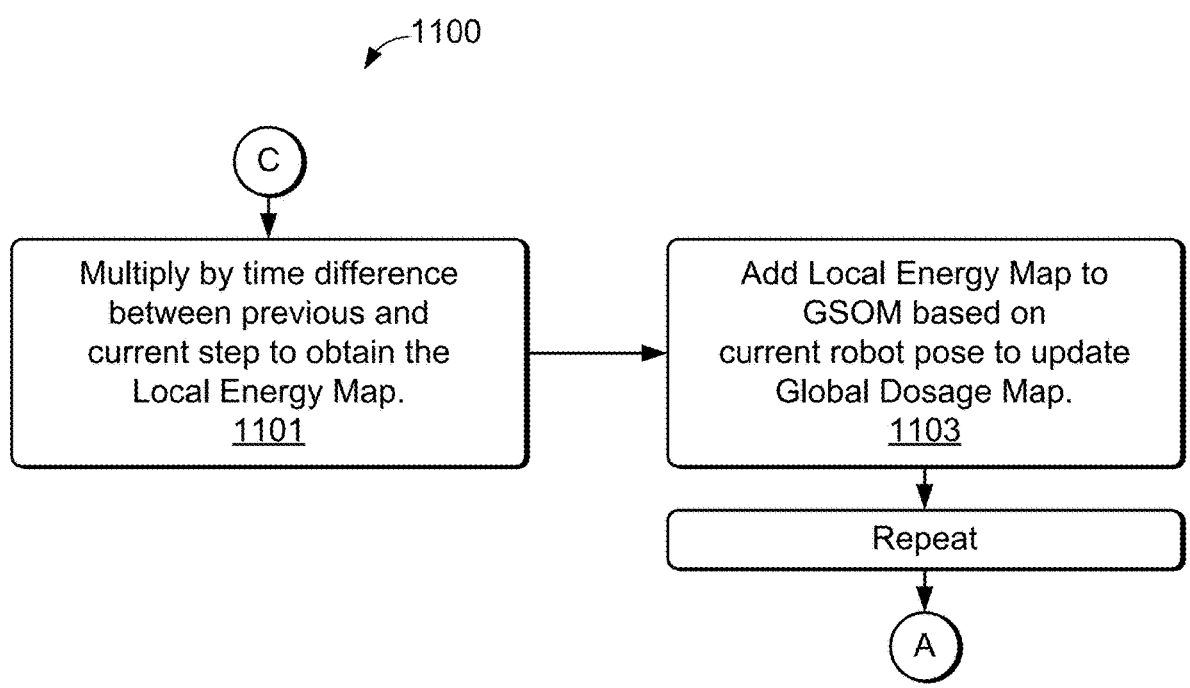
FIG. 11 is a further continuing flow chart the process in accordance with FIG. 9.

From stage 1013, the process 1000 moves on to the process 1100 of FIG. 11. At stage 1101 of the process 1100, the power at each point is multiplied by the steps spent at a particular location to obtain the Local Energy Map. The Local Energy Map is added to the GSOM based on current robot pose to update Global Dosage Map (GDM) at stage 1103. At this point, the process returns to entry point A of the process 900 of FIG. 9 to be repeated while the robot is operating and performing disinfection.

In some cases it is not possible or desirable to plan a path manually prior to use for the robot to execute. It is more desirable that an autonomous path is now planned automatically to deliver the required dosage on all UVC-accessible surfaces in a given spatial map. In an embodiment, this process begins with the generation of a global disinfection costmap. The goal of the process is to enable to the robot to deliver the required dosage on all the surfaces of interest, while preferably not delivering a higher dosage than needed to avoid energy waste and to avoid damage to the materials present in the room that are sensitive to UVC radiation, such as for example some types of plastic.

There are two opposing factors for the automatic planning of an autonomous trajectory of a UVC disinfection robot, namely, the diminishment of optical power with inverse square law and the maneuverability limits of the robot. With respect to the diminishing optical power, it will be appreciated that optical power from a light source decreases quadratically with distance from a light source (inverse square law). Ideally, to achieve maximum energy efficiency, the light source should move as close as possible to the surfaces. The propensity of the robot to be as close as possible to the surface can be mathematically modelled as a cost function which increases quadratically with distance from the surface according to the following relation:

$$\text{Intensity} \propto \frac{1}{d^2} \text{ or Intensity} = \frac{K}{d^2}$$

$$\text{Cost}_{UVCpower} = K_1 d^2$$

where d is the distance of a point from its nearest surface on the map. The function $\text{Cost}_{UVCpower}$ is a parabolic curve. The parameter $K_I$ is based on the power of the UVC optical source.

With respect to the maneuverability of the robot, the robot ideally exhibits its full range of movements in a free space. Hence the most preferable path for the robot to move from one point to another in a given map is to navigate in a path with a high degree of free space around it. This means, the robot will try to keep as much distance from the surfaces as possible.

$$\text{Cost}_{manuever} = \frac{1}{f(d)}$$

This implies a very high cost close to the surfaces and very low cost on the free spaces (further away from the surfaces). In the above expression, f( ) is a non-negative function that increases with the distance (d). This function is dependent on the configuration of the robot and its ease of maneuverability (agility).

An optimal disinfection path will lie in a region that is a balance between these two opposing factors. The final disinfection costmap that will be used for automatic planning a path is a normalized weighted sum of these two independent costmaps. It is important to note, this "final disinfection costmap" is not the same as the Global Dosage Delivery map. This costmap is generated internally as part of the algorithm disclosed here to assist the automatic trajectory generation process.

$$\text{Cost}_{disinfection} = w*\text{Cost}_{UVCpower} - (1-w)*\text{Cost}_{maneuver}$$

An important step in autonomous disinfection is to identify/locate the regions of surfaces in a given map. Only after the "surfaces" to disinfect are segmented from the spatial map, can a path can be planned to disinfect these surfaces by a robot. In a hospital operating room, the surfaces could be the outer walls, inner beds and equipment cabinets. It may not be required or necessary to disinfect every surface, or to select certain surfaces of interest for a particular operational session. To this end, the 2D spatial occupancy grid map is converted into set of points (x,y,Z) where Z=0 in a 2D point cloud. From here, known point cloud segmentation algorithms are used. For example, a region-growing algorithm based on local connectivity (closeness of points to each other) and surface smoothness (normal vectors of consecutive points do not vary more than a predetermined limit amount from each other) may be used. The result of the algorithm is that every point on the given GSOM is assigned to a surface. Computer Vision techniques can be leveraged to recognize and segment various types of surfaces like walls, beds, sinks, cabinets, trolleys etc., and choose the surfaces to be disinfected based on the end user requirements.

The area to be disinfected is grouped into multiple curves with defined starting and ending points. Using the $\text{Cost}_{total}$ calculated above, well known and standard path planning algorithms such as the A* path finding algorithm, the optimal path to disinfect a surface is estimated. Such a plan is estimated for every surface region (curve) in a given spatial map. The speed of executing this path is inversely proportional to the target dosage to be delivered. The speed is also based on layout and complexity of the room on which the path has been planned. Presence of more obstacles and deeper surfaces (not directly accessible by the robot) will decrease the speed. For example, if a surface has less depth such as a wall, the robot can drive quickly. But for a surface like a bed, the robot can drive as close as possible to the outer edge, still needing to provide required dosage till the farther edge of the bed. In such case, the robot needs to drive more slowly to ensure the required dosage is delivered across the whole surface.

While executing the plan generated in the above manner, the dosage map may be simultaneously generated as described earlier in relation to FIGS. 9, 10 and 11. After the trajectory is executed by the robot, the dosages delivered on the segmented surfaces is obtained. If less than the required target dosage is estimated on any of the surfaces, the trajectory for those particular surface regions are repeated again as needed to ensure required dosage is delivered on all surfaces of interest.

In some cases it is not possible or desirable to map an area prior to use. If there is no map available prior to use it is also not possible to plan a path manually prior to use for the robot to execute. With respect to disinfection of such an unknown area, i.e., one without a given map or prior path as above, the DiVASLAM algorithm is used, as disclosed here, to provide the required dosage to all surfaces in the previously unmapped area. Simultaneous Localization and Mapping (SLAM) is a known method to generate a global spatial occupancy map (GSOM) by moving a robot with appropriate sensors in an environment to observe it. The state of the art involves fusion of various sensors in the robot such as odometry, IMU, laser scanners (e.g. LIDAR), 2D and 3D cameras etc.

Exploration to automate a robot identifying new areas to map is commonly executed using naive "Frontier exploration strategy". Here the robot tries to move towards Frontiers, which are regions on the boundary between open-space and unexplored space. These "Frontiers" are marked on local sub-maps of the robot's line of sight, generated by the SLAM algorithm which is running in the background when the robot is moving towards new "Frontiers". An example of this approach is given in Yamauchi et al., A Frontier-Based Approach for Autonomous Exploration," Proceedings 1997 IEEE International Symposium on Computational Intelligence in Robotics and Automation CIRA '97.

Herein, the SLAM technique is extended to include efficient UVC disinfection in the process of exploration. This approach combines SLAM, or a similar algorithm for localization and mapping, Frontier Exploration, or a similar algorithm for exploration during localization and mapping, and disinfection costmap-based path planning to minimize energy consumption of the robot to power the UVC lamps, while delivering the required target dosage for a target reduction in specified pathogens.

The disinfection costmap as discussed above is generated for the local map of the current line of sight region of the robot. The robot still performs Frontier exploration, but the motion from the current location to the next "frontier" to be explored will be traversed on the path generated on the disinfection costmap that is generated.

Once the entire exploration is complete and a complete map of the operating area is generated, a dosage delivery map, as discussed above, is created. Surfaces are clustered and for each surface a residual dosage target is calculated. This residual dosage value is the difference between the total target dosage required and the currently delivered target dosage as below:

$$\text{Residual Dosage}_{Target} = \text{Total Dosage}_{Required} - \text{Delivered Dosage}_{Current}$$

Based on this Residual Dosage Target on the generated map, a path is planned to complete the disinfection process. This will ensure the robot keeps exploring the area until the whole area is mapped, while moving as close as possible to the surfaces in the operating environment while exploring and subsequently to finalize disinfection, if needed, by planning a path to deliver the Residual Dosage. In regions of the map where there is no surface within close vicinity of the robot (e.g., within 3 m), the robot may switch off the UVC lamps during the exploration process to be energy efficient, unless the robot is configured to disinfection the ambient air in a room.

There may be regions in an environment that need to be given special/additional coverage during the disinfection process. Surfaces such as hand railings, door knobs, surgical beds, instrument cabinets, instrument tables, walls, floors, toilets etc. can be very important regions of interest for the disinfection process. A deep learning system based on convolutional neural network can be used to operate on the 2D and 3D information from sensors such as cameras and LIDARs to detect and localize such regions in the Global Spatial Occupancy Map (GSOM). Once such surfaces are localized, pre-programmed maneuvers are used by the robot to deliver the proper amount of disinfection dosage.

In addition to the detection of surfaces, computer vision techniques can also be used to identify the properties of detected surfaces that influence the UVC dosage delivery in the environment. For example, a CV system may be trained to detect the material of surfaces such as textile, vinyl, plastic, metal etc. This is important as these material properties have different UVC absorption, reflection and transmittance properties. For example, some metallic surfaces reflect UVC light, and rough surfaces create micro-shadows which affect the dosage received in surrounding regions. Extensive metal surfaces, e.g. of aluminum, known to reflect UVC light may also be of interest and be used to enhance the modelling (ray casting) of the dosage delivery of UVC radiation in the GSOM.

As noted above, closed loop disinfection may be attained using wireless UVC sensors placed in the room. A wireless UVC sensor is a low power device which can measure the irradiance ($mW/cm^2$) and dosage ($mJ/cm^2$) of UVC light and can communicate such measurements to external devices using e.g., Bluetooth or WiFi wireless communication systems. In closed loop disinfection in an embodiment of the disclosed principles, the robot communicates with such sensors that are placed at one or more key points in an area to be disinfected. These sensors provide the robot with a measurement of the actual amount of dosage received at the location of the sensor. This information is continuously used by the robot's path planning algorithms to ensure the desired dosage target is delivered and to correct and optimize the lamp power distribution models disclosed in this invention to be more accurate and adapted over time to account for example for degradation of the UVC lamps.

The data from such sensors is also be used as proof samples as a part of Quality Control in a further embodiment. In particular, the data from such sensors is placed in a disinfection report generated by the robot after each disinfection task.

As noted earlier herein, one limitation of UVC-based disinfection is that areas where light do not reach cannot be disinfected. In an embodiment, autonomous disinfection by a robot includes identification of such surfaces (in 2D or 3D) where insufficient UVC dosage was delivered. The robot will use this information in its path planning mechanisms to minimize such areas. The robot will also identify regions where the light cannot reach due to physical restrictions (such as obstacles) and mark such regions in the final Global Dosage Delivery map. This map can then be used by human operators to manually apply UVC light, or other means of disinfection such as wipes with suitable chemicals or cleaning agents, in such areas to increase terminal disinfection coverage.

In an embodiment, a human operator executes such a task efficiently via the use AR glasses, where the digital information from the 2D or 3D Global Dosage Delivery map is overlaid in the view of the room. In a further variation of the embodiment the operator can use AR glasses to visualize the disinfection process as the robot is operating and carrying out the disinfection process by one of the methods disclosed herein, thereby making the invisible process of disinfection visible to the end user. Such AR glasses can also be used to clearly and directly provide visual instructions for the operator regarding which areas still need disinfection. The actions of the operator can also be registered by the AR glasses by using known means to register body motion and in particular hand motion to obtain an estimate of the disinfection actions and quality performed by the human cleaning staff. This additional information can be combined with the Global Dosage Delivery map from the robot to provide a final total Global Dosage Delivery map or disinfection map to the end user for record keeping as an audit trail of performed disinfections.

Figure 12:
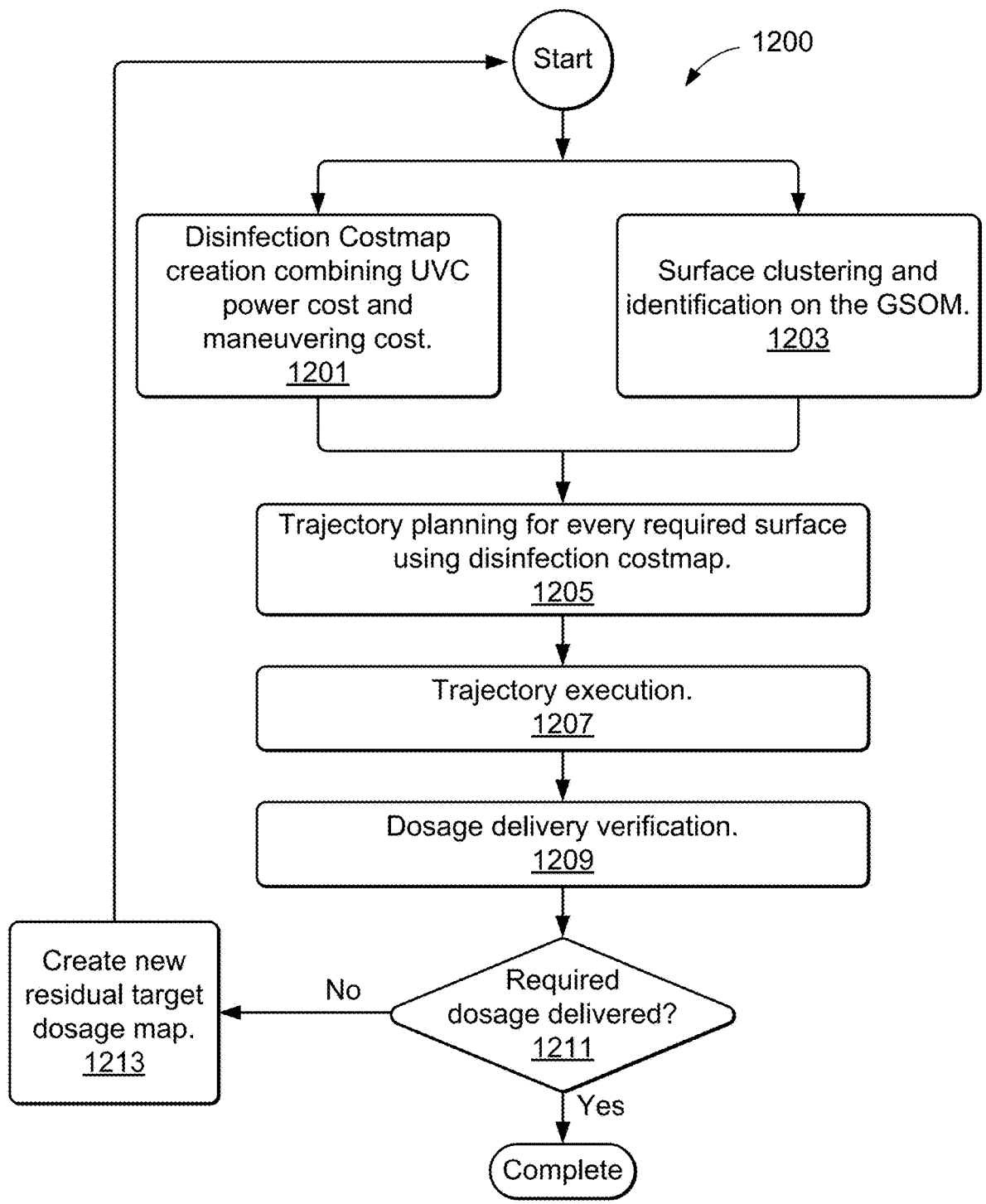
FIG. 12 is a flow chart of another process in accordance with an embodiment of the disclosed principles.

FIG. 12 is a flow chart of another such process. The process 1200 illustrated in FIG. 12 begins at stage 1201 with the creation of a disinfection costmap combining UVC power cost and maneuvering cost. In parallel at stage 1203, surface clustering and identification on the GSOM is executed.

Figure 14A:
FIG. 14A is a sample 2D area map.
Figure 14B:
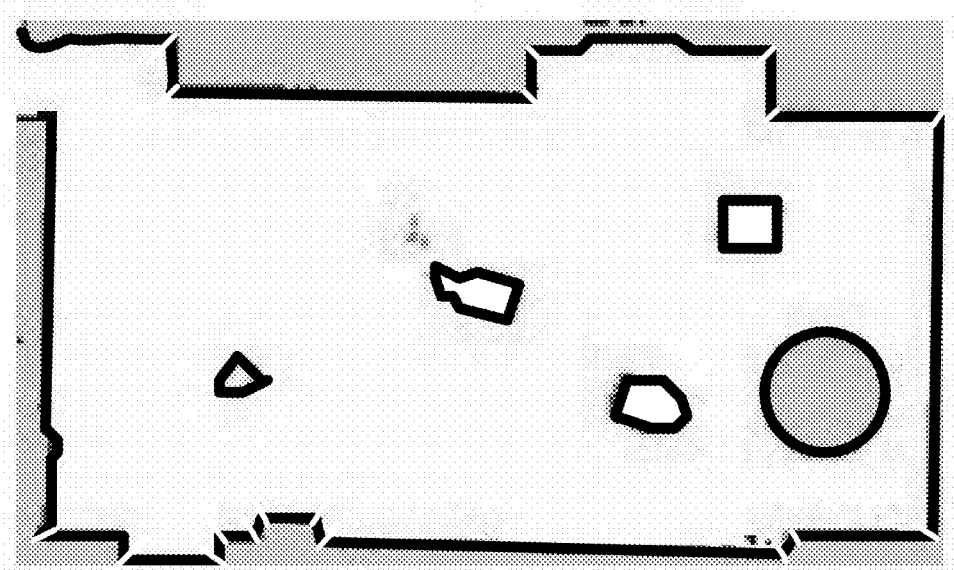
FIG. 14B is the sample 2D area map of FIG. 14A with curves clustered into surfaces in accordance with an embodiment of the disclosed principles.

FIGS. 14A and 14B show the result of surface clustering in the 2D map case. In particular, FIG. 14A represents a 2D area map and FIG. 14B represents the same area with curves clustered into surfaces (solid lines separated by white).

Figure 15:
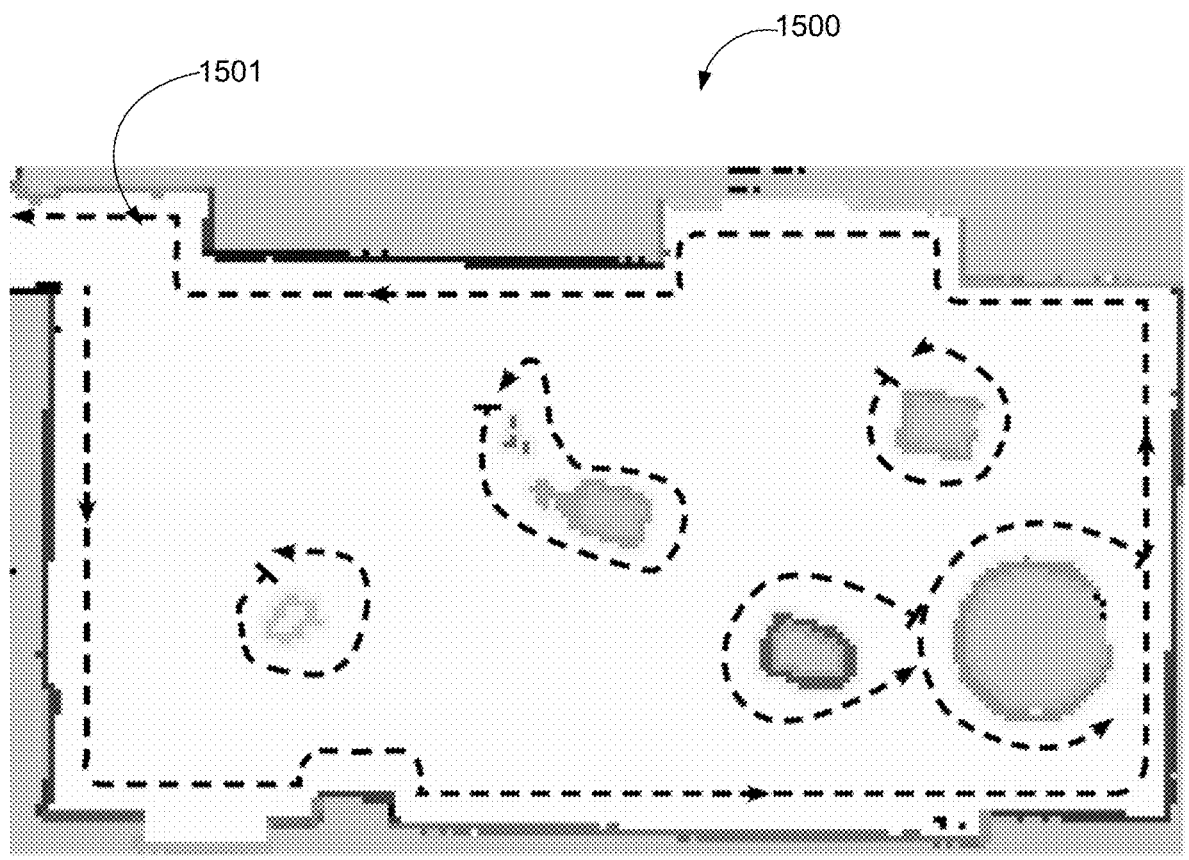
FIG. 15 is an example trajectory in accordance with an embodiment of the disclosed principles.

Continuing with the process 1200 of FIG. 12, a trajectory is planned for every required surface at stage 1205 using the disinfection costmap, and the trajectory is executed at stage 1207. An example trajectory 1501 is shown via the map 1500 of FIG. 15.

Continuing, the dosage delivery is verified at stage 1209 and the process then moves to stage 1211 wherein a check is run to confirm that the required dosage will be delivered. If the check at stage 1211 shows that the required dosage will be delivered, then the process completes. Otherwise, the process flows to stage 1213 to create a new residual target dosage map before returning to start again.

Figure 13:
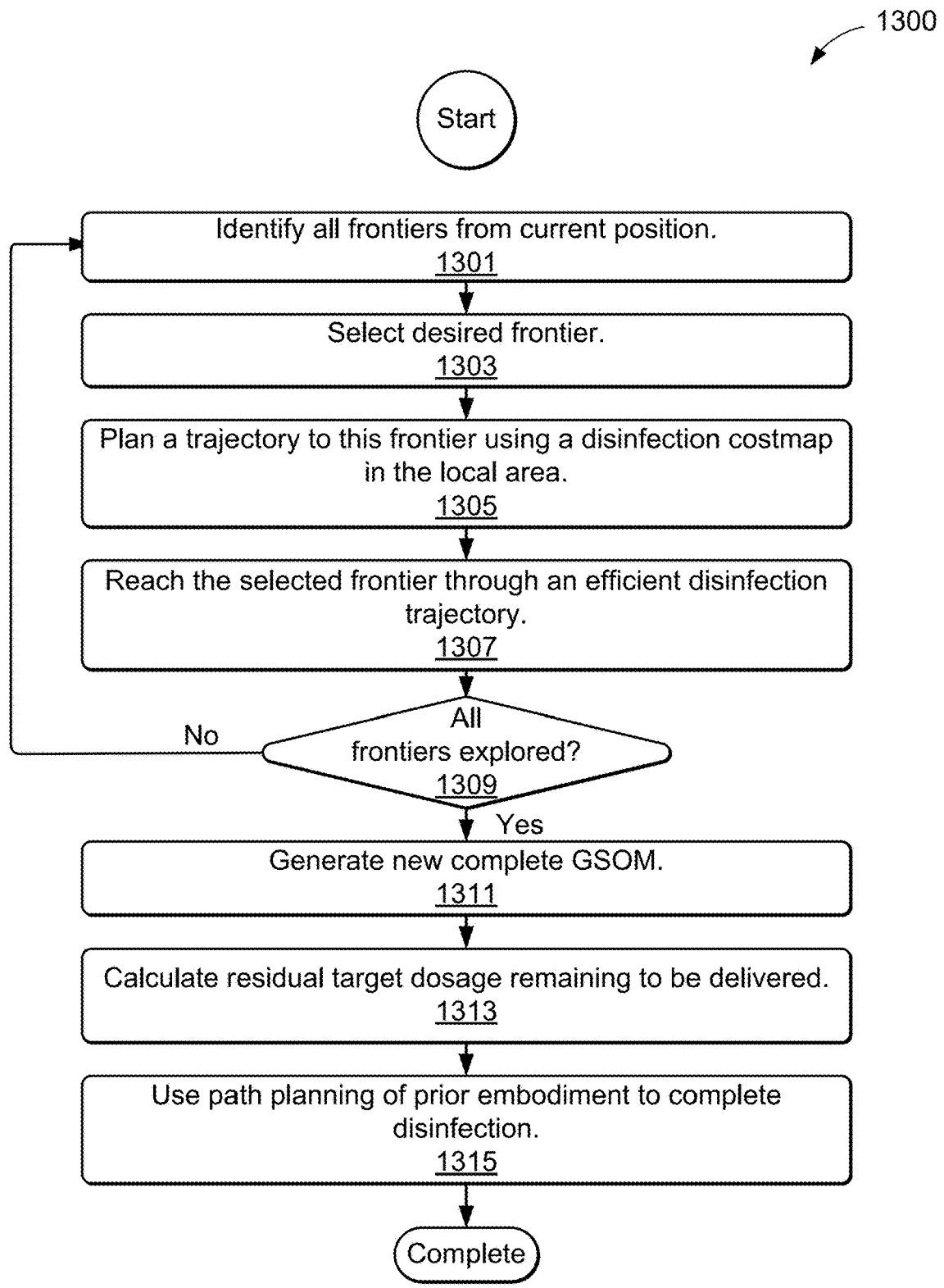
FIG. 13 is a flow chart of yet another process in accordance with an embodiment of the disclosed principles.

FIG. 13 is a flow chart in accordance with an embodiment of the disclosed principles. The process 1300 starts at stage 1301, wherein all available frontiers are identified from the robot's current position. The desired frontier is then selected at stage 1303 and at stage 1305, a trajectory to this frontier is planned using a disinfection costmap in the local area. The selected frontier is then reached via an efficient disinfection trajectory at stage 1307. If all frontiers have not yet been explored, as checked at stage 1309, then the process 1300 returns to stage 1301. Otherwise, the process 1300 moves forward to stage 1311, wherein a new complete GSOM is generated. The residual target dosage remaining to be delivered is calculated at stage 1313, and disinfection is completed using the path planning of FIG. 13 at stage 1315. At this point, the process 1300 is complete.

It will be appreciated that various systems and processes have been disclosed herein. However, in view of the many possible embodiments to which the principles of the present disclosure may be applied, it should be recognized that the embodiments described herein with respect to the drawing figures are meant to be illustrative only and should not be taken as limiting the scope of the claims. Therefore, the techniques as described herein contemplate all such embodiments as may come within the scope of the following claims and equivalents thereof.

We claim:

1. A robot-executed method of disinfection of a site by an autonomous movable robot equipped with at least one germicidal UVC light source, the method comprising:
   using an exploration strategy to move within the site to generate a map and disinfection costmap of the site in 2D or 3D, while performing disinfection of surfaces;
   generating a trajectory based on the disinfection costmap, wherein the trajectory considers a need to explore and map the site, power consumption and shadow areas; and
   while performing disinfection, generating a global dosage delivery map in 2D or 3D based on the executed trajectory and consequent shadow areas.

2. The method in accordance with claim 1, wherein the trajectory further ensures that a given maximum dosage is not surpassed, so as to protect materials in site from photo degradation.

3. The method in accordance with claim 1, wherein the robot uses computer vision as part of the exploration strategy to automatically identify space and surfaces of interest to disinfect.

4. The method in accordance with claim 1, wherein the robot uses computer vision as part of the exploration strategy to automatically identify optical properties of surface materials to improve estimation of global dosage delivery map by accounting for reflection of UVC light from certain surfaces.

5. The method in accordance with claim 1, wherein the global dosage delivery map is 3D, further comprising displaying the global dosage delivery map in AR (augmented reality) or VR (virtual reality) to support an operator in identifying shadow areas for additional disinfection.

6. The method in accordance with claim 5, further comprising updating the global dosage delivery map by tracking the manual actions performed by the operator carrying out manual disinfection.

7. The method in accordance with claim 1, further comprising using a wireless UVC sensor to update an illumination distribution model of the robot, to account for changes in UVC output power.

8. A robot-executed method of site disinfection by an autonomous movable robot equipped with at least one germicidal UVC light source, the method comprising:
   generating a disinfection costmap based on a given site map in 2D or 3D for the robot to disinfect the space and surfaces of interest in the site while considering shadow areas and power usage;
   generating a disinfection trajectory based on the disinfection costmap;
   causing the robot to autonomously execute disinfection of the site by navigating substantially along the disinfection trajectory while activating the at least one germicidal UVC light source; and
   recording the actual dosages delivered in a global dosage delivery map in 2D or 3D including shadow areas which have not received sufficient dosage, while the robot autonomously executes disinfection of the site.

9. The method in accordance with claim 8, wherein the trajectory further ensures that a given maximum dosage is not surpassed, so as to protect materials in site from photo degradation.

10. The method in accordance with claim 8, wherein the robot uses computer vision to automatically identify space and surfaces of interest to disinfect.

11. The method in accordance with claim 8, wherein the robot uses computer vision to automatically identify optical properties of surface materials to improve estimation of the global dosage delivery map by accounting for reflection of UVC light from surfaces.

12. The method in accordance with claim 8, wherein the global dosage delivery map is 3D, the method further comprising displaying the global dosage delivery map in AR (augmented reality) or VR (virtual reality) to support an operator in identifying shadow areas for additional disinfection.

13. The method in accordance with claim 12, further comprising updating the global dosage delivery map by tracking the manual actions performed by the operator carrying out manual disinfection.

14. The method in accordance with claim 8, further comprising using a wireless UVC sensor to update an illumination distribution model for the robot, to account for changes in UVC output power.

15. A robot-executed method of site disinfection by an autonomous movable robot equipped with at least one germicidal UVC light source, wherein the site is represented in a map in 2D or 3D, having associated therewith a trajectory, the method comprising:
   autonomously navigating the site by the robot substantially along the trajectory while activating the at least one germicidal UVC light source; and
   generating a global dosage delivery map in 2D or 3D based on an actual trajectory executed by the robot, wherein the global dosage delivery map includes any shadow areas which have not received sufficient dosage.

16. The method in accordance with claim 15, wherein the actual trajectory deviates from the trajectory associated with the map due to the robot deviating from the trajectory associated with the map upon encountering an obstacle.

17. The method in accordance with claim 15, wherein the robot uses computer vision to automatically identify optical properties of surface materials to improve estimation of the global dosage delivery map by accounting for reflection of UVC light from surfaces.

18. The method in accordance with claim 15, wherein the global dosage delivery map is 3D, the method further comprising displaying the global dosage delivery map in AR (augmented reality) or VR (virtual reality) to support an operator in identifying shadow areas for additional disinfection.

19. The method in accordance with claim 18, further comprising tracking the manual actions performed by the operator carrying out manual disinfection.

20. The method in accordance with claim 15, wherein a wireless UVC sensor is used to update an illumination distribution model for the robot, to account for changes in UVC output power.

\* \* \* \* \*